US011635785B2

(12) United States Patent
Kariguddaiah (10) Patent No.: US 11,635,785 B2
(45) Date of Patent: Apr. 25, 2023

(54) SMARTWEARABLES WITH EMBEDDED NFC (NEAR FIELD COMMUNICATION) AND VITAL HEALTH SENSORS WITH MOBILE/CLOUD DATA AND ULTRA VIOLET GERMICIDAL IRRADIATION (UVGI) TECHNOLOGIES

(71) Applicant: Abijith Kariguddaiah, Danville, CA (US)

(72) Inventor: Abijith Kariguddaiah, Danville, CA (US)

(73) Assignee: Abijith Kariguddaiah, Danville, CA (US)

( * ) Notice: Subject to any disclaimer, the term of this patent is extended or adjusted under 35 U.S.C. 154(b) by 141 days.

(21) Appl. No.: 16/904,996

(22) Filed: Jun. 18, 2020

(65) Prior Publication Data

US 2021/0397213 A1     Dec. 23, 2021

(51) Int. Cl.
| | | |
|---|---|---|
| *G06F 1/16* | (2006.01) | |
| *A61L 2/10* | (2006.01) | |
| *A61L 9/20* | (2006.01) | |
| *H04W 4/80* | (2018.01) | |
| *A61B 5/00* | (2006.01) | |
| *H04W 4/38* | (2018.01) | |
| *A61B 5/024* | (2006.01) | |

(52) U.S. Cl.
CPC .......... *G06F 1/163* (2013.01); *A61B 5/02438* (2013.01); *A61B 5/6804* (2013.01); *A61L 2/10* (2013.01); *A61L 9/20* (2013.01); *H04W 4/38* (2018.02); *H04W 4/80* (2018.02)

(58) Field of Classification Search
CPC ....... G06F 1/163; A61B 5/02438; A61L 9/20; H04W 4/38; H04W 4/80
See application file for complete search history.

(56) References Cited

U.S. PATENT DOCUMENTS

| | | | | |
|---|---|---|---|---|
| 9,117,327 | B1* | 8/2015 | Wasil | G06Q 20/1085 |
| 9,597,004 | B2* | 3/2017 | Hughes | G16H 50/20 |
| 10,695,530 | B1* | 6/2020 | Surace | A61M 21/02 |
| 2014/0312834 | A1* | 10/2014 | Tanabe | H02J 50/001 |
| | | | | 320/108 |
| 2015/0172441 | A1* | 6/2015 | Samhat | H04M 1/72448 |
| | | | | 455/418 |

(Continued)

*Primary Examiner* — Said Broome
(74) *Attorney, Agent, or Firm* — Abijith Kariguddaiah (57) ABSTRACT

The smart wearable with embedded NFC (Near Field Communication) tags, vital health sensors and UV-C germicidal irradiation sources is provided for Prevention of spread of pathogens. The smart wearables is any of a hand glove, a footwear, a vest, a full body suit, a face mask, a footwear cover or a smart portables where all the smart wearables includes a plurality of re-programmable tags to facilitate touch less activities, and a plurality of body health monitoring sensors to monitor health of the wearer in real time for early warning health mechanisms, an Ultraviolet Germicidal Irradiation (UVGI) source to disinfect the surfaces coming in contact with the smart wearables with maximum efficacy and spread prevention. Further, the inner layer of the smart wearables which makes contact with the skin of the wearer is made of a Celliant synthetic polymer fabric material that traps the body's infrared energy and cycle it back to improve oxygenation and resolve minor aches and pains.

14 Claims, 12 Drawing Sheets

(56) References Cited

U.S. PATENT DOCUMENTS

| | | | | |
|---|---|---|---|---|
| 2015/0297134 A1* | 10/2015 | Albert | .................... | A61B 5/681 |
| | | | | 600/509 |
| 2016/0103503 A1* | 4/2016 | Pham | .................... | G06F 3/0208 |
| | | | | 345/170 |
| 2019/0209806 A1* | 7/2019 | Allen | .................... | A61M 21/02 |

* cited by examiner

SMARTWEARABLES WITH EMBEDDED NFC (NEAR FIELD COMMUNICATION) AND VITAL HEALTH SENSORS WITH MOBILE/CLOUD DATA AND ULTRA VIOLET GERMICIDAL IRRADIATION (UVGI) TECHNOLOGIES

FIELD OF THE INVENTION

The present invention relates to the smart wearable for preventive health outcomes and lifesaving. More particularly, it is a smart wearable having an NFC embedded technologies for 'No-Touch' operations, a plethora of health monitoring sensors providing early warning mechanism via Mobile/Cloud and an Ultraviolet Germicidal Irradiation (UVGI) source that disinfects the surface area where the wearer touches after wearing the smart wearable.

BACKGROUND OF THE INVENTION

As the world is facing outbreak of Covid-19, one of the biggest pandemic of a century, a contagious disease that is being spreads from person to person either by direct touch of infected person, through air when the infected person sneezes or coughs or by touching or using something an infected person has touched or used. One can protect him/herself up to some extent by washing hands well often, following social distancing norms and staying away from those who are sick.

But, not all these options are there for front line warriors such as doctors, healthcare workers, average citizen, elderly, Military servicemen, and Public servants' etc. as they are all always at constant risk from infection form their daily activities. In addition of being at constant risk of getting infected, the healthcare workers and doctors for example are also a significant factor in disease transmission from patient to patient by virtue of inadequate attention to, or inadequate technology for, sanitization. As the healthcare professionals go from patient to patient, they can transport pathogens present over their body, hands, clothing, other wearables, footwear, products and healthcare items they touch, etc. One touch of a hand or any part of a body having pathogens alive on it may contaminate all the surfaces coming in contact with it. For example, when the health care workers and physicians open doors, handle equipment while wearing gloves, they could be contaminating the doors if the pathogen exists on the user's hands/glove, or picking up the pathogen from the door handle. And since the virus can be present when the infected doesn't have any symptoms, makes it even more of a critical challenge.

Furthermore, these wearable cannot be washed easily while being worn, also they are not replaced as often as should be to limit the transmission of disease and constant replacement of the wearable increases costs associated with the patient care. Thus, one of the effective method to disinfect the germs before it reaches the human body is by causing the germs' inability to replicate and exposure of pathogens to ultraviolet radiation has proven to be effective in causing the germs' inability to replicate, and this has been researched and proven by the professors at New York based Columbia university, and specifically on Covid-19.

Therefore, during this emergency situation of covid-19 pandemic, there exists a dire need of a smart wearables having an embedded NFC technology for frontline healthcare workers and others that may limit the need of touching the various surface by the wearer. There further exists a need of a smart wearables having a plethora of health monitoring sensors embedded within the wearables and coupled with the mobile/cloud to continuously update the real time body condition of the wearer, so that preventive care can be taken or enforced, for much superior outcomes than anything else that exists today. Also, there exists a need of a smart wearables having an Ultraviolet Germicidal Irradiation (UVGI) technology that disinfects the surface of the wearable as well as other area that the wearer desires to disinfect using UV-C ultraviolet germicidal light source, preventing not only the spread of the pathogen and also providing for a sense of security to the user and their surrounding environment, providing for better socio-economic outcomes.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The present invention provides a smart wearables with embedded NFC (Near Field Communication) technology, plethora of health monitoring sensors and a UVGI Germicidal technology. The smart wearables of present invention intends to save lives and provide a preventative health outcomes using a plurality of health monitoring sensors that measures a critical data of the wearer such as temperature, blood pressure, Oxygen level, etc. for early detection and prevention of COVID-19 and also other health issues. Secondly, an NFC technology that makes the 'no-touch' condition possible as the wearer just needs to point the NFC tags present within the smart wearables towards the NFC readers to facilitate many touch less activities such as opening doors or getting access without touching, answering calls or making payments, etc. in a present like emergency situations which could become the new-normal, where social distancing and avoiding touching to any unnecessary surface is a key requirement.

Thirdly, the UV-C germicidal irradiation (UVGI) technology is provided to make the wearer capable of disinfecting the surface area that comes into contact with the smart wearables. The smart wearables of present invention is embedded with a UVGI light source ranging from 200 nm to 400 nm for various applicable wearable use case scenarios that disinfects any bacteria and/or pathogens coming in contact with the wearable thus protecting the wearer from any infection, disinfecting any area the wearer touches hence protecting others touching the same area or clearing the pathogens from said area, and stopping the spread of the infection making for a much safer environment.

According to one embodiment, the smart wearable further includes a proximity and a pressure sensor as a safety sensors configured to turn On the smart wearables only when the user grabs something with certain amount of pressure, and/or only when within close proximity (less than 1-5 cms) of the touch area, thereby protecting the wearer from any UVGI exposure.

The UVGI technology of present invention has proven to be effective against SARS-I and MERS, a similar virus strains to Covid-19 (also called SARS-II), and hence it is effective against Covid-19 too. The UV-C radiation of the UVGI technology modifies the RNA/DNA and eliminates the ability of the pathogens to reproduce and the pathogens that can't reproduce are not infectious, and are therefore harmless. The UVGI of the present smart wearables are capable of deactivating pathogens such as, but not limited to, Influenza, the common flu, anthrax, smallpox, viral hemorrhagic fever, pneumonic plague, tularemia and drug resistant tuberculosis.

According to one embodiment, the smart wearables are any of the gloves, shoes, vest, full body suit, face mask, footwear cover or any smart portables having all the above mentioned features embedded within the wearables, including the Smart Glove, ensures that all the surface area of the touch area required to do any particular activity such as a hold, handshake, clasp, grab, etc., receives 100% UVGI radiation such that 100% of the users touches-surface area, are disinfected ensuring maximum EFFICIENCY and EFFICACY of the UVGI mechanism, providing best case safety scenarios for user environment.

According to one embodiment, the smart wearables are any of the gloves, shoes, vest, full body suit, face mask, footwear cover or any smart portables having all the above mentioned features embedded within the wearables, including the Smart Mask, ensures that all the air that the user breathes through the face mask, is filtered through the UVCI irradiation light sources, thereby disinfecting the air breathed, making it safer for the user, reducing infection risk.

According to one embodiment, the smart wearables are any of the gloves, shoes, vest, full body suit, face mask, footwear cover or any smart portables having all the above mentioned features embedded within the wearables, including the Smart Footwear/Footwear cover, ensures that all the stepped on/walked on area where the user treads, is constantly being disinfected with the UVGI light sources, reducing the spread of the infection for others who may tread on the same spots later, thereby constantly disinfecting the floor area proportional to the no of users wearing said wearables in said space, thereby reducing infection risk.

According to one embodiment, the smart wearables are any of the gloves, shoes, vest, full body suit, face mask, footwear cover or any smart portables having all the above mentioned features embedded within the wearables, including the Smart Vest/Full Vest/Body Suit, ensures that all the external things that come into contact with the users clothing, if they lean on a desk, patients bed, sitting on a chair, etc., all being constantly disinfected during their daily activities, using the safe UVGI light source, making for a constantly improving safe environment for all parties. Furthermore, the were cab disinfectant any item by exposing the item against their vest UVGI source, making it a personal mobile and portable disinfectant unit, further reducing infection risk. And providing for peace of mind.

According to one embodiment, the smart wearables are any of the gloves, shoes, vest, full body suit, face mask, footwear cover or any smart portables having all the above mentioned features embedded within them, therefore providing the ability to the wearer to disinfect anything hence not only offers germicidal safety to user, but also an important means of preventing the spread of infection and germs, and over constant usage over time, makes the user environment more and more safer.

According to one embodiment, the plethora of health monitoring sensors of the smart wearable tracks reading with accuracy including temperature, blood oxygenation level, blood pressure, heart rate, etc. and provides that real time readings over a mobile applications via a cloud technology that allows of the patient historic data to the care providers to provide a better care. This makes possible, an early detections, warnings and hence aids in preventing the spread of a disease. Additionally, the smart wearables of present invention includes an EKG sensor, a pulse detection sensor and other health monitoring sensors. Over time, an establishment may now have enough data on the user/wearer such that new technologies including Machine Learning/Artificial Intelligence may produce better outcomes to both the user, their insurers, and establishments.

The inner layers of the smart wearables, according to one embodiment, that makes contact with the skin is made of a Celliant synthetic fabric material which is known to trap the body's infrared energy and cycle it back to improve oxygenation within the body as well as resolve minor aches and pain.

In healthcare facilities, the smart wearables facilitates the healthcare workers and physicians to use NFC technology to open doors, answer calls etc. without touching anything and just by waving their hand or by pointing a tag present within any of the smart wearable such as gloves or shoes or vest to a specific NFC reader for any practical purpose. While, at the same time, the wearer can disinfect any surface, such as the door handle or any other product or equipment by touching or making a contact of the smart wearable with the surface which needs to be disinfected.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF INVENTION

The embodiment herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the method and embodiments herein may be practiced and to further enable those of skill in the art to practice the embodiments herein. Accordingly, the examples should not be construed as limiting the scope of the embodiments herein.

The disclosure of present invention provides a smart wearables to save lives by preventing spread of infection from day-to-day activities, to facilitate early detection and tack of potential infections, to work as a PPE equipment for the frontline healthcare and defense workers, to work as a digital key to open doors, operate smartphones, card exchange etc. without touching anything, and to disinfect any surface, product or equipment using the smart wearables. According to one embodiment, the smart wearables of present invention includes all the body wearable such as, but not limited to, a hand gloves, a foot wear, a face mask, a footwear cover, a body wear i.e. a vest, a full body suit or any other portable means. All the smart wearables of present invention are embedded with: a plethora of health vital sensors to monitor real time body health condition of the wearer; a re-programmable NFC (near field communication) tags that allows wearer to do many things without having to touch any surface; an Ultraviolet Germicidal Irradiation (UVGI) light sources to disinfect any surface that wearer touches or walks on, or desires to disinfect; and a celliant fabric as an inner layer where the skin comes in contact with the wearables, where the celliant fabric traps the body's infrared energy and cycles it back within the body to improve oxygenation and resolves minor aches and pains.

According to one embodiment, the smart wearables of present invention might also work as a smart PPE for front line health care workers who are at constant risk from infections. The plethora of health or vital sign monitoring sensors of the smart wearables continuously monitors and reports the real time body health condition to hospital system and to the healthcare professionals, therefore saves lives by early detection and prevention of the spread of the pathogens such as covid-19 which can be deciphered based on increase in body temperature and/or measuring oxygen levels in the blood.

According to one embodiment, the smart wearables of present invention is comprising of a sensors such as, but not limited to, a temperature sensor, a blood oxygenation sensor, a blood pressure or pulse detection sensor, an EKG and other popular sensors as the industry proliferates. The smart wearables of the present invention further includes an electronic control units having a communication module that collects the data from all these sensors, compares it with pre-defined limits and sends the warning or alert signal over the mobile applications to the person of concern to prevent the spread of an infection. Further, the electronic control unit of the smart wearables stores the data over the cloud to create a historic data set for the caregivers to deliver better outcomes.

According to one embodiment, the smart wearables of present invention further includes a safety sensors such as a proximity sensor and a pressure sensor that are configured to turn on the smart wearables only when the wearer grabs or touches something with certain amount of pressure, thereby protecting the wearer from any UV light exposure issues.

The re-programmable NFC chips and tags embedded within the smart wearables are configured to allow user to do many touch activities without having to touch any surface that might be contaminated by the infection like answering phones, opening or closing doors, sending social media messages, payment mechanism, etc. Further, the NFC tags are re-programmable and hence can be programmed to do specific functions in conjunction with the localized NFC readers.

According to one embodiment, the Ultraviolet germicidal irradiation (UVGI) light sources of different strength are provided within the smart wearables of present invention to disinfect the area coming in contact with the surface of the smart wearables. The UV-C radiation of the UVGI sources modifies the RNA/DNA and eliminates the ability of a pathogen to reproduce. The pathogen that can't reproduce are not infectious, and are therefore harmless. The effectiveness of UVGI derives from a band of UV-C radiation centered at a wavelength of 265 nm plus or minus 60 nm.

Furthermore, the smart wearables are any of the gloves, shoes, vest, full body suit, face mask, footwear cover or any smart portables having all the above mentioned features embedded within the wearables, including the Smart Glove, ensures that all the surface area of the touch area required to do any particular activity such as a hold, handshake, clasp, grab, etc., receives 100% UVGI radiation such that 100% of the users touches-surface area, are disinfected ensuring maximum EFFICIENCY and EFFICACY of the UVGI mechanism, providing best case safety scenarios for user environment.

Figure 1A:
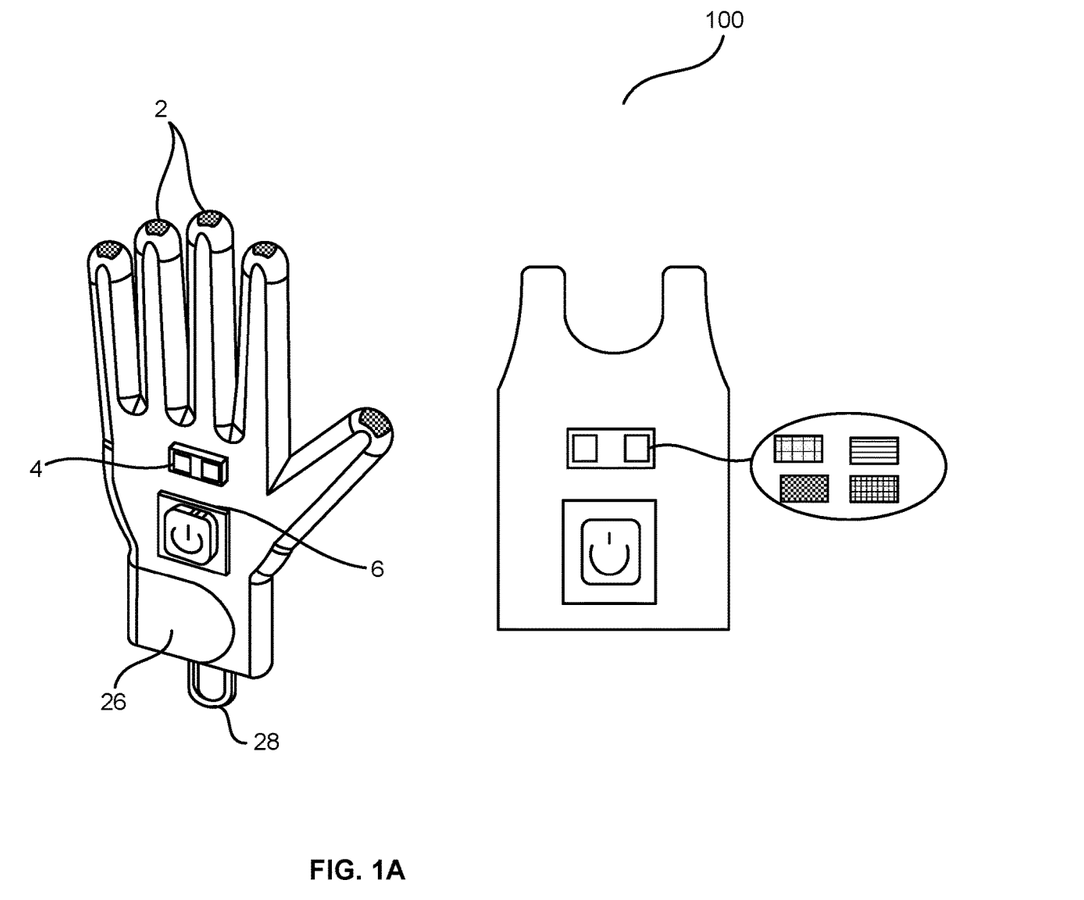
FIG. 1A shows a back view of a smart hand glove as a smart wearable of present invention.

Now, referring to FIG. 1A that shows a back view of a smart hand glove 100 as a smart wearable of present invention. According to present embodiment, the smart glove 100 is comprising of an NFC tags 2 embedded within each and all the fingertips of the smart glove 100. A sensory unit 4 having a plurality of various sensors such as a blood temperature sensor, a blood oxygenation sensor, a proximity and pressure sensors, and a motion sensor to respectively monitor the blood temperature, oxygen level, distance and pressure over the glove 100 and provide for a safety feature, and a movement of all angles of an Wrist or ankle. According to one embodiment, an electronic control unit 6 is also configured within the smart glove 100 that works as a brain of the smart gloves that manages power distribution to all the other electronic components, collects data from the sensors, identifies the risk or emergency situation from the sensory data and accordingly sends alert signals to the mobile application of the person of concern as well as stores the data over the cloud for future reference. This cloud data may be accessed by the user, the establishment, and/or the doctors for better outcomes. According to one exemplary embodiment, the smart glove 100 of present invention may further comprise a strap 26 to close the glove 100 securely over the hand and a strap 28 to pull glove onto hand.

Figure 1B:
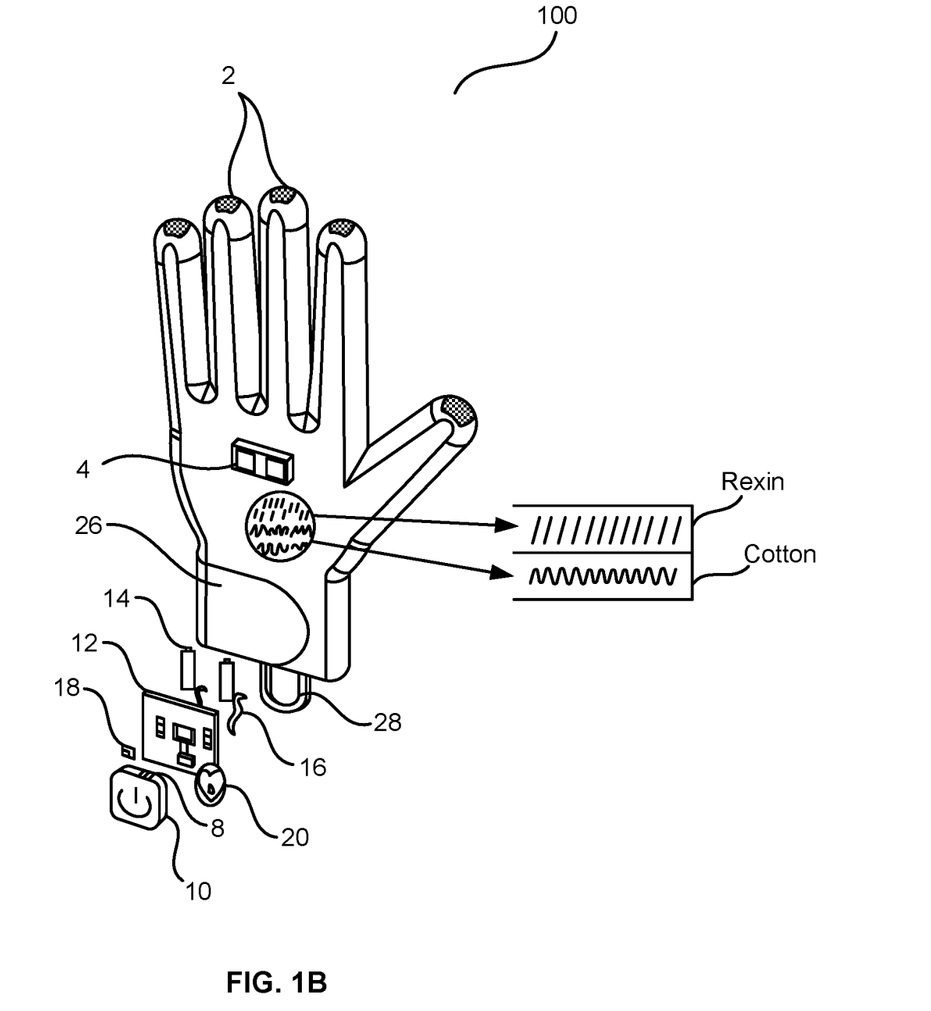
FIG. 1B shows a same back view of a smart glove with an exploded view of an electroniccontrol unit.

FIG. 1B shows back view of a same smart glove 100 with an exploded view of an electronic control unit 6. According to present embodiment, the electronic control unit is further comprising of; a touch screen 8 with a power switch 10 on screen 8 that is configured to allow wearer to manually start or stop working of the smart glove 100 or to manipulate operation of the smart glove 100 using the touch screen 8; a printed circuit board 12 having a micro controller and a communication module, where the micro controller allows for the power management of the different type of light sources user within the smart wearables, drives the touch screen for various functions including powering the device, safety controls, collects the data from all the sensors, uploads that data over a cloud for future reference, determines the emergency condition and sends the alert signal over the mobile application of a person of concern.

The electronic control unit 6 of present invention is further comprising of a rechargeable batteries 14 to provide power for functioning of all the electronic components of the smart wearable 100. A wire 16 that connects the electronic components with the electronic control unit 6. According to one embodiment, a temperature sensor 18 and a blood pressure or pulse detection sensor 20 is configured within the electronic control unit to respectively monitor body temperature and a pulse rate of the wearer.

Figure 2:
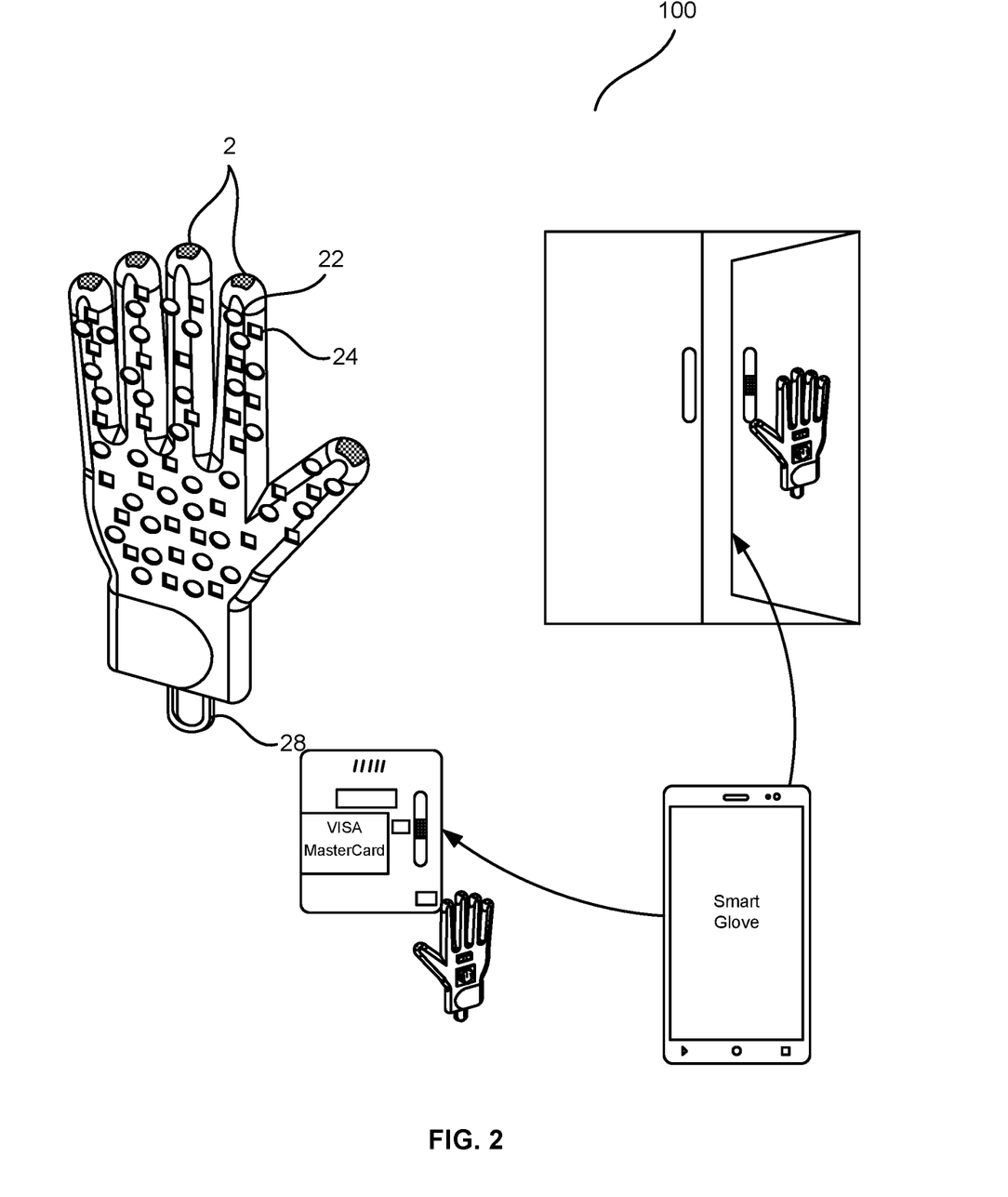
FIG. 2 shows a front view of the smart glove disclosed in FIGS. 1A and 1B of present invention denoting the 'No-Touch' functions in conjunction with the localized NFC readers.

FIG. 2 shows a front view of the smart glove 100 disclosed in FIGS. 1A and 1B of present invention also denotes the purpose of NFC tags at fingertips via one embodiment where it can be used to pay at Shops and also to open doors to do specific 'No-Touch' functions in conjunction with the localized NFC readers.

Figure 3:
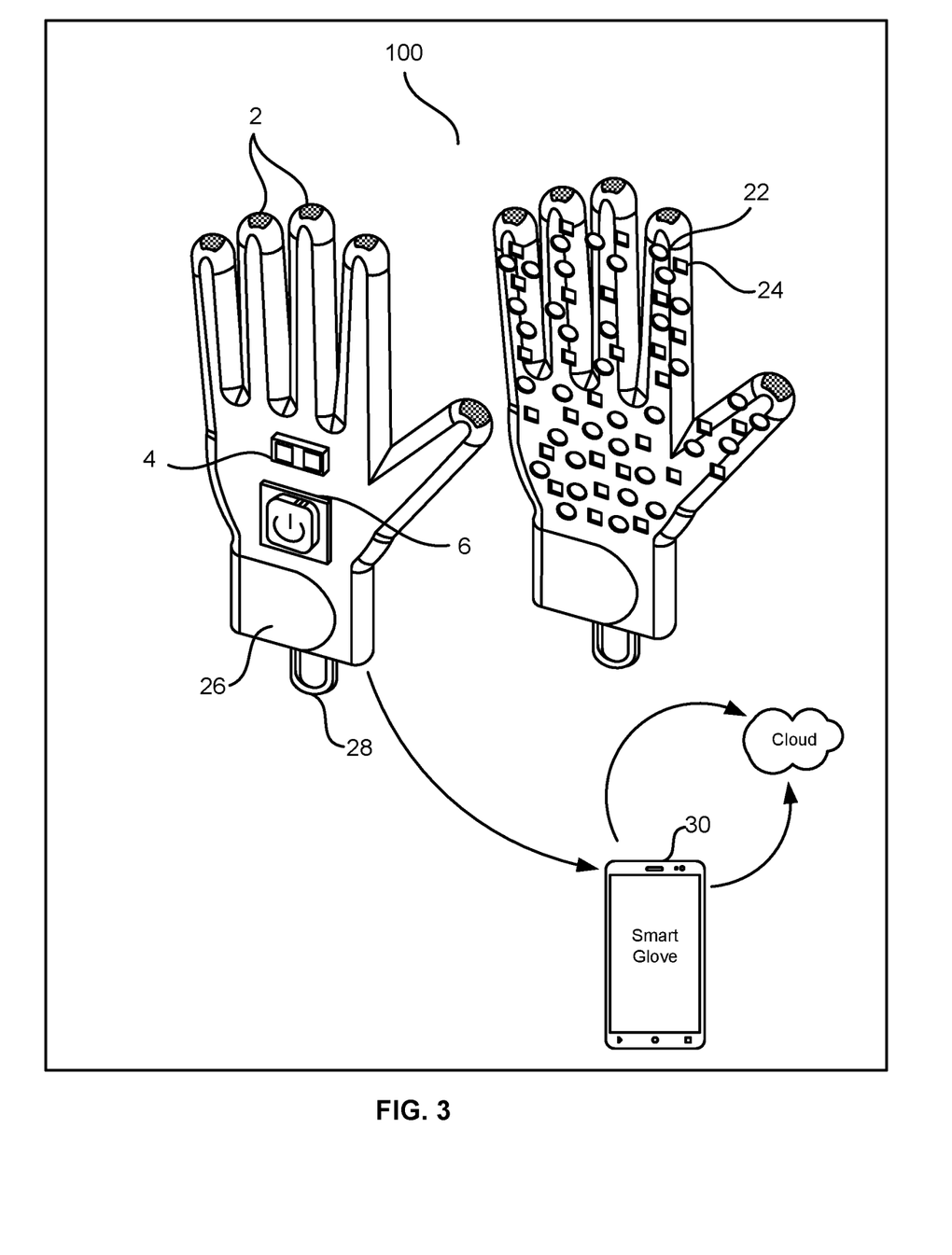
FIG. 3 shows complete system of smart wearable having both the gloves and a smart user device having mobile application.

FIG. 3 illustrates an exemplary embodiment of pair of a smart gloves 100 as a smart wearable of present invention along with monitoring using the mobile application 112 installed within the smart device 30. According to one embodiment, the electronic control unit 6 allows connectivity of the smart wearables with the mobile application 30. The mobile application 112 allows user and caregivers to monitor the real time health data from the sensors as well as allows re-programming of the NFC tags to do specific 'No-Touch' functions in conjunction with the localized NFC readers. The mobile application further allows user to access and/or share the cloud in future to get the historic data set.

Figure 4:
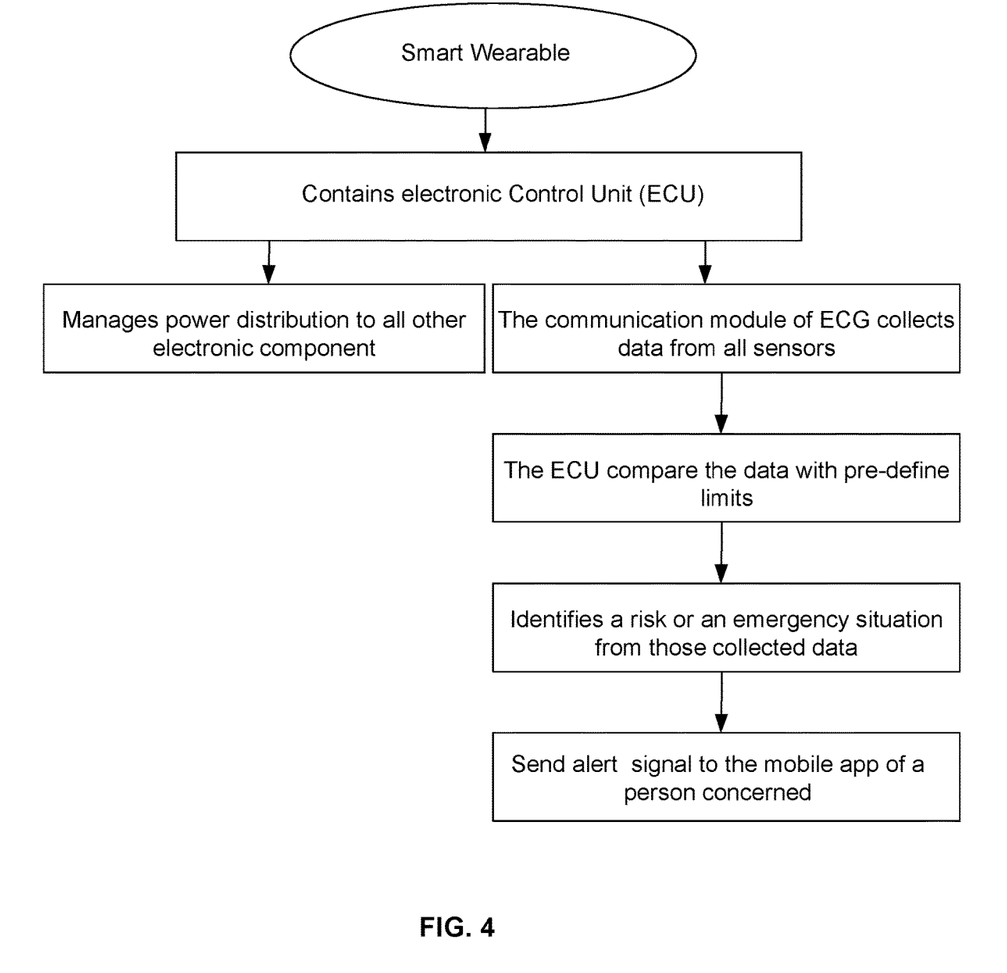
FIG. 4 is a flow diagram depicting step by step hierarchical functioning of smart wearable's.

FIG. 4 is a flow diagram depicting step by step hierarchical functioning of smart wearable's containing the electronic control unit which manages power distribution to all other electronic component and simultaneously collects, compares, identifies data from all sensors and sends alert signal to the mobile app, as part of an embodiment of the invention.

Figure 5A:
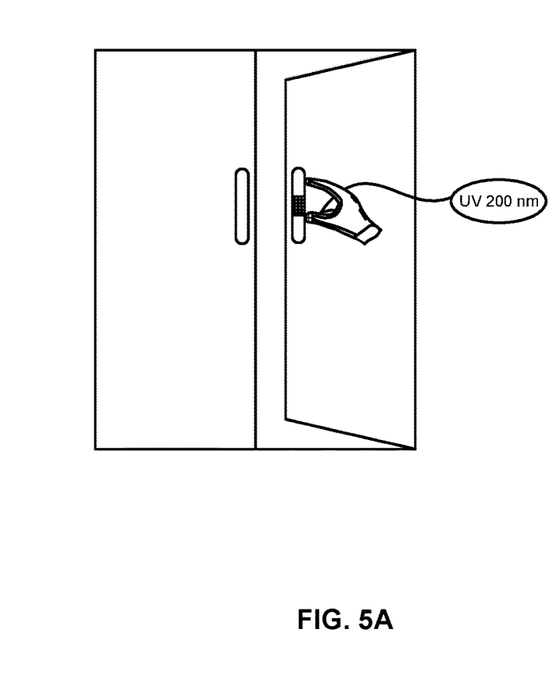
FIG. 5A and 5B exemplarily illustrates an embodiment where a glove is used to open the door at the same while disinfecting that touch area with UV irradiation.
Figure 5B:
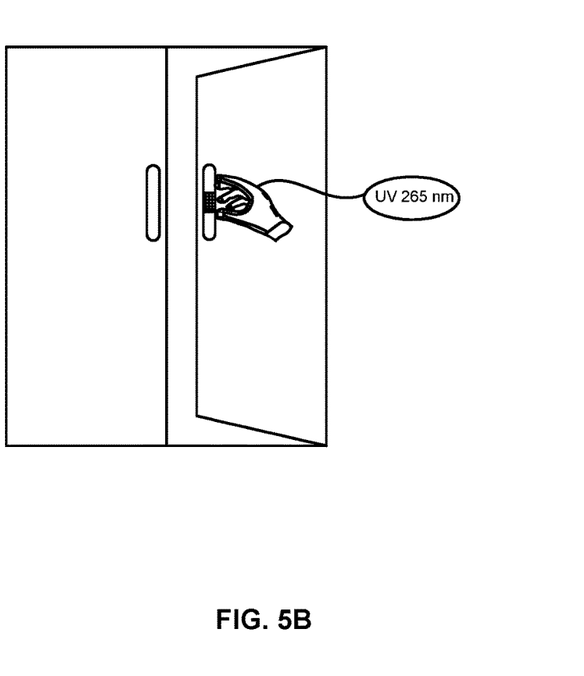

FIG. 5A and FIG. 5B exemplarily illustrates the smart glove 100 includes plurality of UV-C light sources 22 and 24 of respective intensity of 200nm and 265nm, in one embodiment, mounted within the palm area of the glove such that all the surface area touched by the person for any touch, grab, hold activity may receive UV irradiation to disinfect whole area.

Figure 6:
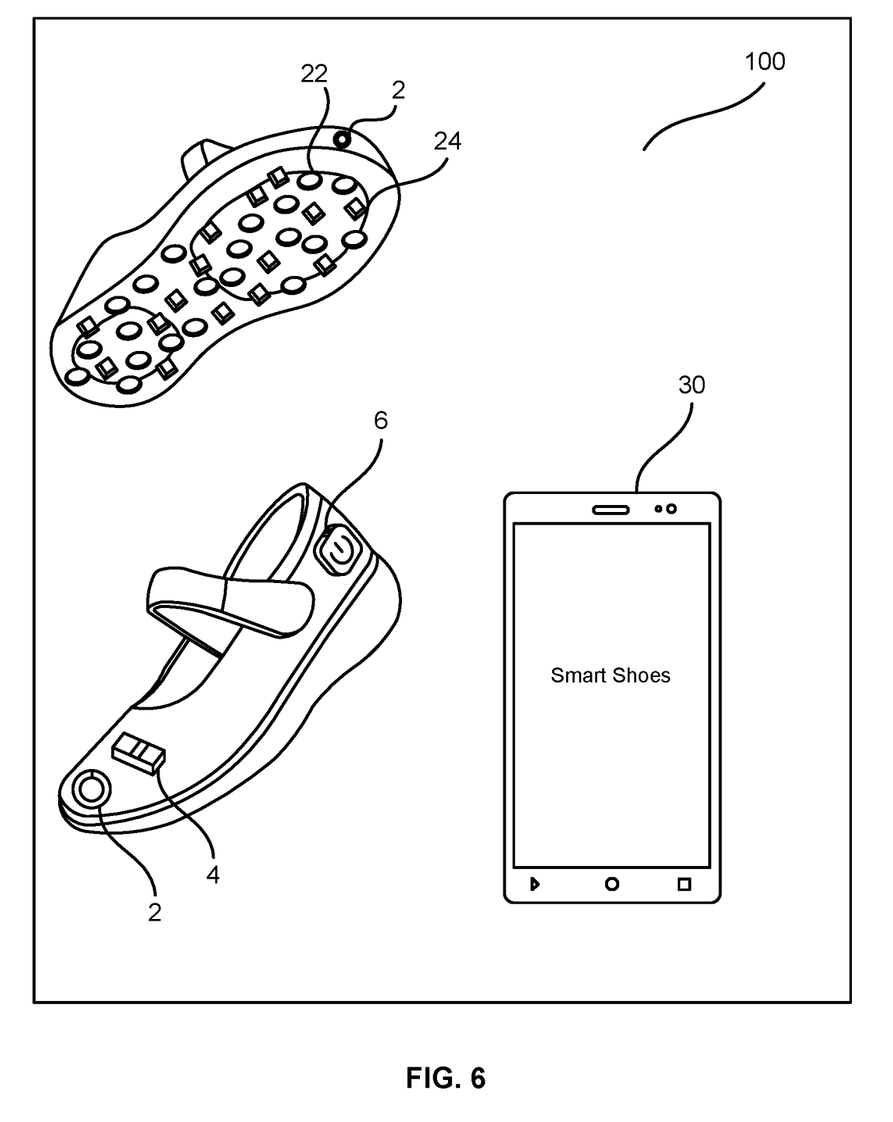
FIG. 6 illustrates an exemplary embodiment of a smart shoes as a smart wearable of present invention along with monitoring using the mobile application.

FIG. 6 illustrates an exemplary embodiment of a smart shoes 100 as a smart wearable of present invention along with monitoring using the mobile application 112. For the sake of easy understanding, all the smart wearables shown in figures are numbered with the same number 100. According to present invention, the smart shoes also comprises all the components that were present in the smart glove. The smart shoe 100 also comprises an NFC tags 2 mounted at front point of the shoe 100; a sensory unit 4 having plurality of various sensors on the top portion; an electronic control unit 6 on the sides of the shoe 100 and a plurality UVGI (UV-C) light sources 22 and 24 mounted within the sole at the bottom of the smart shoes 100.

Figure 6A:
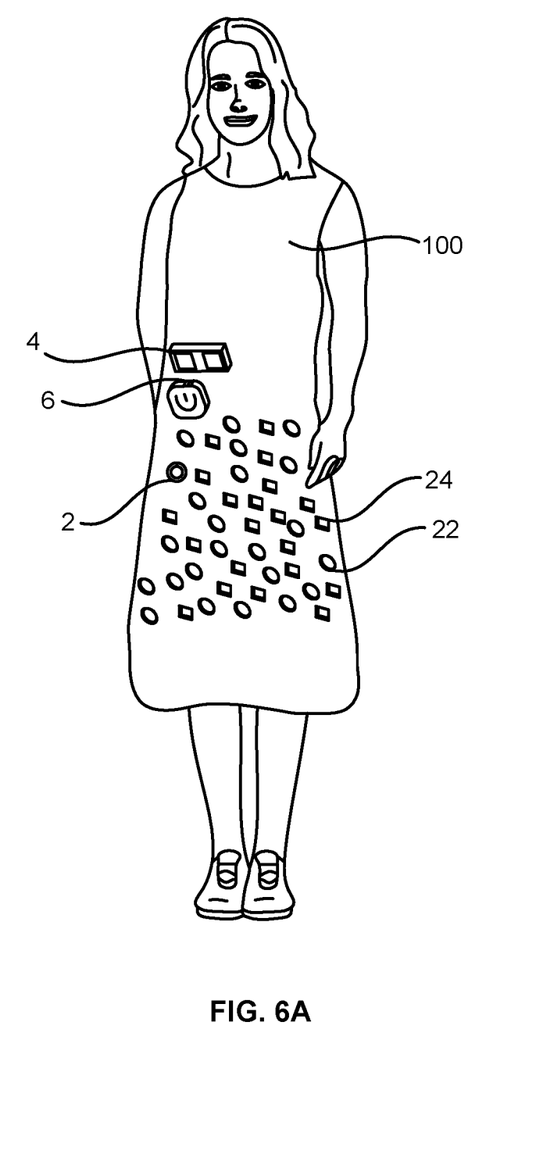
FIG. 6A exemplarily illustrate an embodiment of a smart half vest as a smart wearable of present invention.
Figure 6B:
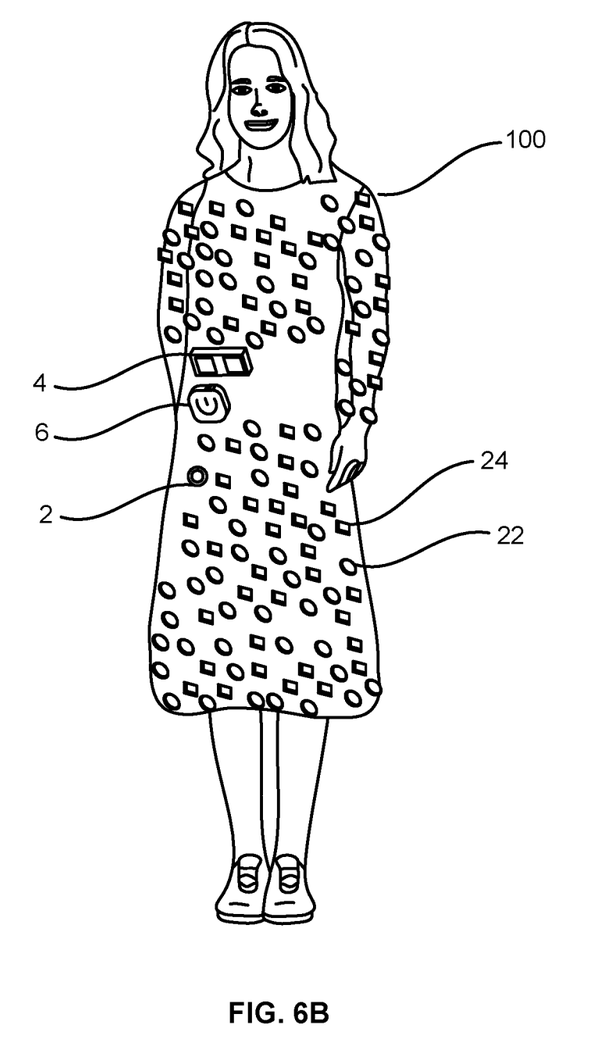
FIG. 6B exemplarily illustrate an embodiment of a smart full vest as a smart wearable of present invention.
Figure 7:
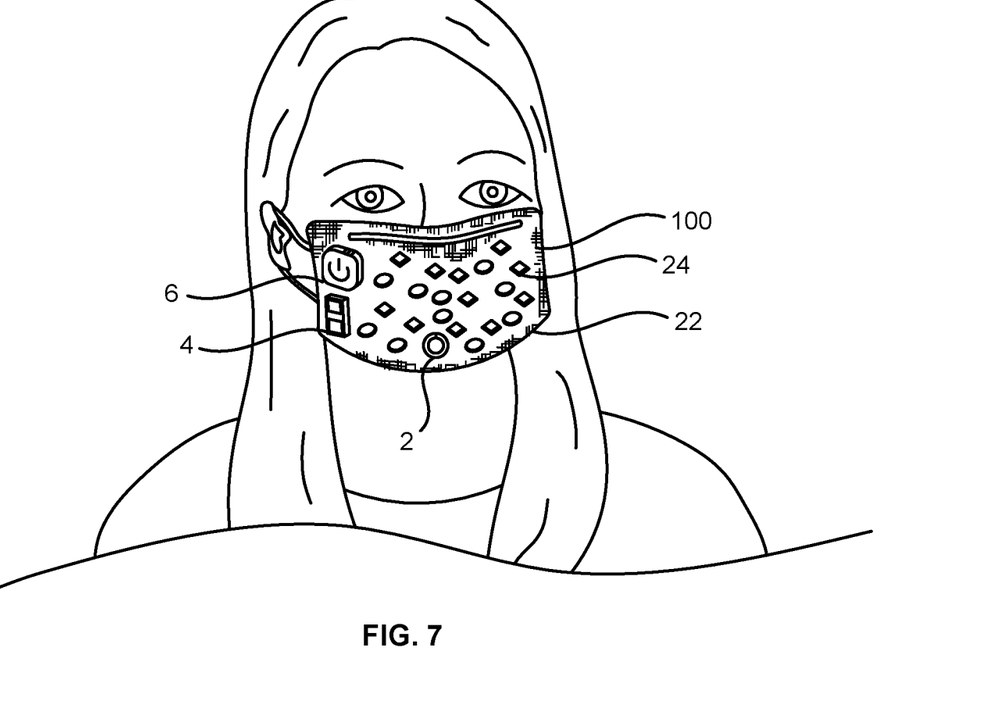
FIG. 7 exemplarily illustrates an embodiment of a face mask as a smart wearable of present invention.

FIG. 6A and FIG. 6B exemplarily illustrate an embodiment of a smart half vest 100 and smart full vest 100 respectively as a smart wearable of present invention that are also comprising of all the components of the smart wearables mounted at different location within the smart vest 100. While, FIG. 7 illustrates and embodiment of a smart face mask 100 as a smart wearable of present invention comprising all the novel component and functional features same as other smart wearables of present invention.

Figure 7A:
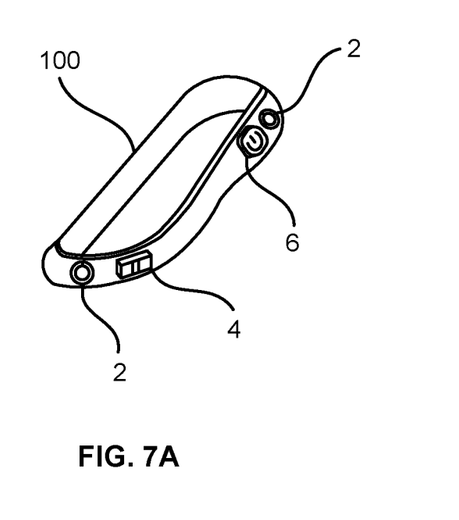
FIG. 7A and FIG. 7B exemplarily illustrates an embodiment of a shoe cover worn over the shoes for temporary purposes as a smart wearable of present invention.
Figure 7B:
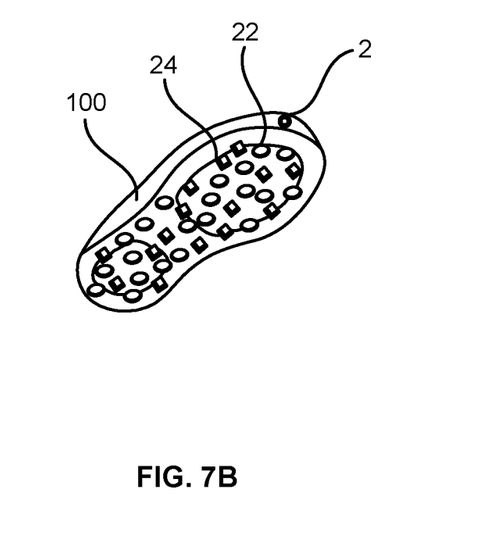

FIG. 7A and FIG. 7B exemplarily illustrates an embodiment of a shoe cover 100 as a smart wearable of present invention. According to this embodiment, it allows any user to wear this smart cover on any shoes for temporary use, instead of wearing a user specific smart shoes. The shoes cover also includes all the components such as an NFC tags 2, a sensory unit 4, an electronic control unit 6, a UVGI light sources and all the other components same as other smart wearable of present invention.

Figure 8:
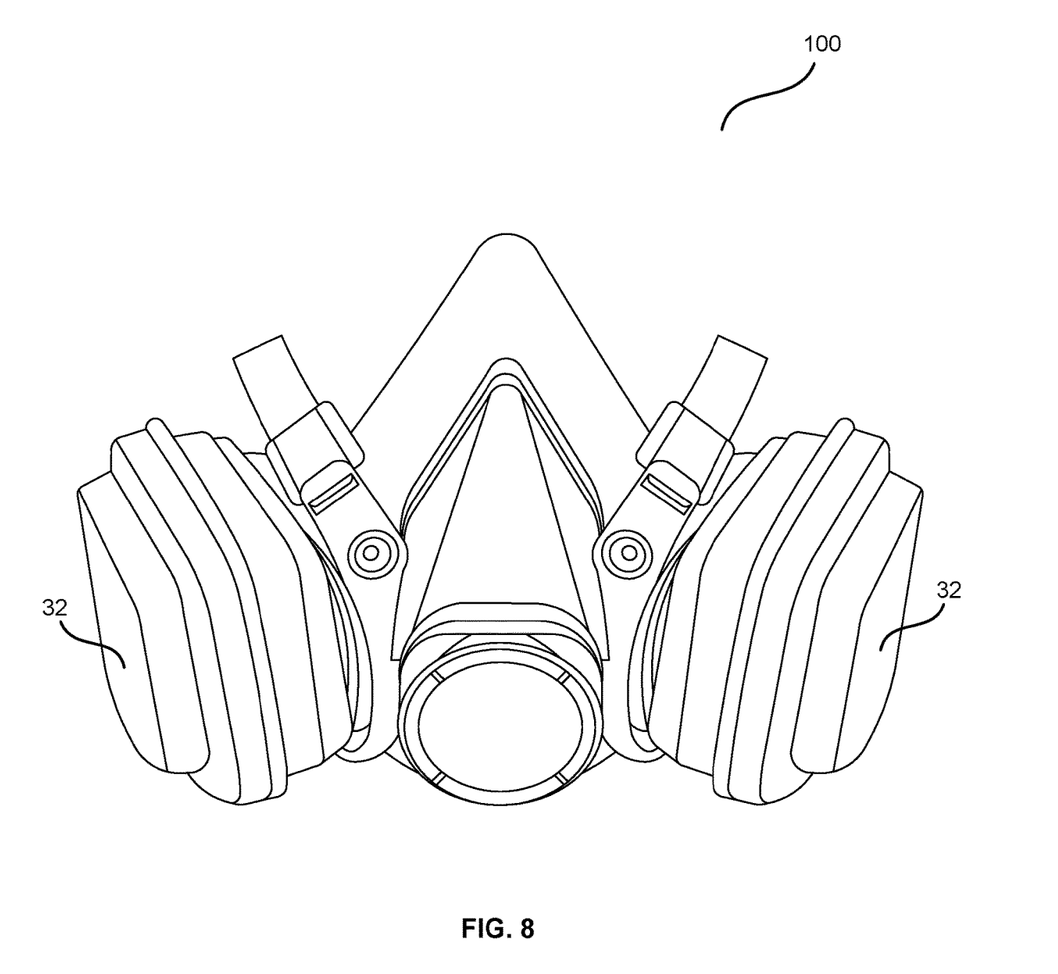
FIG. 8 illustrates one another exemplary embodiment of the face mask wherein the UVGI source is contained within the external protected air-inlet protrusion.

While, FIG. 8 illustrates one another exemplary embodiment of the face mask 100 wherein the UVGI source is contained within the external protrusions 32 instead of direct embedding within the body of the smart wearables. According to one embodiment, the face mask 100 is comprising of all the other components same as other smart wearables and includes a pair of separate external protrusions 32 having a UVGI light sources where the external protrusions 32 encloses the UVGI light sources to prevent unnecessary exposure of the UVGI radiation. According to one embodiment, all the smart wearables of present invention are ergonomic, thin, waterproof, and washable for reuse and can be disinfected using common disinfectants.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A multifunctional smart wearables for preventing pathogen spread and saving lives is comprising of:
   a plurality of different health monitoring sensors embedded within the multifunctional smart wearables to monitor real time body health condition of a wearer;
   a plurality of re-programmable NFC (near field communication) tags mounted within the multifunctional smart wearables;
   an Ultraviolet Germicidal Irradiation (UVGI) light source mounted over an exterior surface of the multifunctional smart wearables; and
   an electronic control unit having a communication module to collect the data from the sensors and stores the data over cloud which is further comprising of:
   a touch screen with a power switch;
   a printed circuit board having a microcontroller and a communication module; and
   a rechargeable batteries,
   wherein the electronic control unit stores a sensory data over a cloud to create a historic data set for future reference.

2. The multifunctional smart wearables of claim 1 is any wearable such as a smart glove, a smart half or full vest, a smart footwear, a face mask, a smart footwear cover or a smart full body suit.

3. The multifunctional smart wearables of claim 1, wherein the smart wearables provides maximum efficacy for a touch surface area for the UVGI disinfection.

4. The multifunctional smart wearables of claim 1, wherein the smart wearables are ergonomic, thin, waterproof, and washable for reuse.

5. The multifunctional smart wearables of claim 1, wherein the plurality of different health monitoring sensors includes a temperature sensor, a blood pressure, a blood oxygenation sensor, a blood pressure sensor, an EKG sensor, and a pulse detection sensor.

6. The multifunctional smart wearables of claim 1, wherein the re-programmable NEC tags are configured to allow the wearer to do touch activities Without having to touch any surface.

7. The multifunctional smart wearables of claim 1, wherein the NFC tags are re-programmable NFC tags allows use of the same NFC tags for different purposes in different multifunctional smart wearables.

8. The multifunctional smart wearables of claim 1, wherein the re-programmable NFC tags allows re-programming to do a specific functions in conjunction with a localize NFC readers.

9. The multifunctional smart wearables of claim 1, wherein the Ultraviolet Germicidal Irradiation (UVGI) light sources are configured to disinfect any surface with maximum efficiency and efficacy for any daily activity that the wearer touches or walks on, or desires to disinfect.

10. The multifunctional smart wearables of claim 1, wherein the Ultraviolet Germicidal Irradiation (UVGI) light sources are of different strength and intensity used for a different wearable use cases.

11. The multifunctional smart wearables of claim 1, wherein the electronic control unit is configured to manage a power distribution to all the other electronic components, to collect the sensory data, to identify a risk or an emergency situation from the sensory data and accordingly sends alert signals to the mobile application of a person of concern.

12. The multifunctional smart wearables of claim 1, is further comprising of a proximity and a pressure sensor as a safety sensor which are configured to turn ON the UVGI light sources only when the wearer grabs or touches something with certain amount of pressure.

13. The multifunctional smart wearables of claim 1, wherein an interior surface of the multifunctional smart wearable is made of a Celliant synthetic fabric that traps the body's infrared energy and cycle back to improve an oxygenation within the body as well as resolves minor aches and pain.

14. The multifunctional smart wearables of claim 1, wherein the control unit is further comprising of a touch screen with power switch, a micro controller, memory, a communication module and a rechargeable battery.

* * * * *